US012630955B2

(12) United States Patent (10) Patent No.: US 12,630,955 B2
Saffold (45) Date of Patent: May 19, 2026

(54) PORTABLE MASK CLEANING DEVICE

(71) Applicant: David Saffold, Indianapolis, IN (US)

(72) Inventor: David Saffold, Indianapolis, IN (US)

( * ) Notice: Subject to any disclaimer, the term of this patent is extended or adjusted under 35 U.S.C. 154(b) by 381 days.

(21) Appl. No.: 18/121,984

(22) Filed: Mar. 15, 2023

(65) Prior Publication Data

US 2024/0309571 A1 Sep. 19, 2024

(51) Int. Cl.
| | |
|---|---|
| *D06F 13/02* | (2006.01) |
| *A61L 2/18* | (2006.01) |
| *D06F 39/02* | (2006.01) |
| *D06F 11/00* | (2006.01) |
| *D06F 18/00* | (2006.01) |
| *D06F 105/56* | (2020.01) |

(52) U.S. Cl.
CPC ................ D06F 13/02 (2013.01); A61L 2/18 (2013.01); D06F 39/022 (2013.01); *D06F 11/00* (2013.01); *D06F 18/00* (2013.01); *D06F 2105/56* (2020.02)

(58) Field of Classification Search
CPC ............. A61L 2/18; D06F 13/02; D06F 11/00
See application file for complete search history.

(56) References Cited

U.S. PATENT DOCUMENTS

| | | | | |
|---|---|---|---|---|
| 2,639,601 | A | * | 5/1953 | Miller ..................... D06F 37/14 |
| | | | | 68/210 |
| 2,680,367 | A | | 6/1954 | Dougherty |

| | | | | |
|---|---|---|---|---|
| 4,522,045 | A | | 6/1985 | Harada |
| 5,570,598 | A | | 11/1996 | Haven |
| 6,393,725 | B1 | | 5/2002 | Smith |
| D749,804 | S | | 2/2016 | Ha |
| 2005/0005655 | A1 | | 1/2005 | Taylor |
| 2008/0236621 | A1 | | 10/2008 | Lin |
| 2012/0222453 | A1 | * | 9/2012 | Mueller .................. D06F 45/12 |
| | | | | 68/13 R |
| 2013/0074882 | A1 | * | 3/2013 | Ackermann ......... A62B 23/025 |
| | | | | 134/103.3 |
| 2018/0209084 | A1 | * | 7/2018 | Chakravarty ........... D06F 58/04 |

FOREIGN PATENT DOCUMENTS

| | | | | | |
|---|---|---|---|---|---|
| CN | 111228545 | A | * | 6/2020 | ............... A61L 2/26 |
| CN | 114367339 | A | * | 4/2022 | ............... B02C 4/02 |
| DE | 102023209959 | B3 | * | 11/2024 | ............... A46B 3/16 |
| WO | WO2012060477 | | | 10/2012 | |

* cited by examiner

*Primary Examiner* — Michael E Barr
*Assistant Examiner* — Kevin G Lee

(57) ABSTRACT

A portable mask cleaning device for washing and drying face masks includes a housing. A slot has a conduit protruding into an interior of the housing. A holding is positioned within the interior has a top wall and a bottom wall. A pair of fins is positioned within the holding where a stepper motor rotates the pair of fins within the holding. A pair of electric coils heats an interior of the holding. A soap container has a tube protruding into the holding. A water container has a tube protruding into the holding. A door is coupled to the bottom wall of the holding where a drain is positioned in a center of the door. A processor is positioned within the interior of the housing to render data and perform operations. An outlet positioned on front surface of the housing is an opening to the interior of the housing.

17 Claims, 5 Drawing Sheets

PORTABLE MASK CLEANING DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to clothing wash device and more particularly pertains to a new clothing wash device for washing and drying face masks.

(2) Description of Related Art Including Information Disclosed Under 37 CFR 1.97 and 1.98

The prior art relates to clothing wash devices. The prior art includes a variety of clothing wash devices being portable wherein moving the clothing wash device is facilitated. Known prior art lacks a clothing wash device being portable and controlled by a mobile device configured for washing and drying face masks.

BRIEF SUMMARY OF THE INVENTION

An embodiment of the disclosure meets the needs presented above by generally comprising a housing having a front surface and a back surface positioned parallel relative to each other. Additionally, the housing has a left surface and a right surface, wherein each of the surfaces enclosing an interior. A slot is positioned on the front surface of the housing. A conduit protrudes out from the slot into the interior of the housing. The conduit has a pair of rollers being configured for moving a face mask through the conduit. A holding is positioned within the interior of the housing. The holding has a top wall and a bottom wall. In addition, the holding has a perimeter wall. The holding is configured for storing the face mask. A pair of fins is positioned within the holding and the pair of fins is coupled to a rod. The rod is coupled to a stepper motor being configured for rotating the pair of fins within the holding. A pair of electric coils is positioned adjacent to the perimeter wall of the holding wherein each of the electric coils is configured for heating an interior of the holding. A soap container is positioned adjacent to the front surface and the right surface of the housing. The soap container has a tube protruding out from the soap container into the top wall of the holding. Furthermore, a water container is positioned adjacent to the front surface and the left surface of the housing. The water container has a tube protruding out from the water container into the top wall of the holding. A door is coupled to the bottom wall of the holding where a drain is positioned in a center of the door. The drain is a conduit from the door to a reservoir. A processor is positioned within the interior of the housing. The processor is configured for rendering data and performing operations of within the interior of the housing. An outlet is positioned on front surface of the housing. The outlet is an opening to the door of the holding of the interior of the housing. A power cord is in electric communication with a power source wherein the power source of the power cord is configured for providing electric power to the processor.

Furthermore, a method for cleaning a mask with a portable device includes the step of plugging an outlet plug of a power cord of the portable device into a power outlet. The user inserts a face mask within a slot of a front surface of a housing of the portable device. A pair of rollers moves the face mask through a conduit to a holding within an interior of the housing. The user actuates a processor of the portable device using a plurality of controls or an application of a mobile device in communication with a transceiver of the processor. The actuation of the processor includes the step of actuating a pump of a tube of a soap container to flow laundry detergent into the holding. Additionally, the processor actuates a pump of a tube of a water container to flow water into the holding. The processor actuates a stepper motor of a pair of fins within the holding. The stepper motor rotates the pair of fins within the holding wherein washing the face mask. The processor removes the fluid from the holding by actuating a pump of a drain to a reservoir. Subsequently, the processor actuates a pair of electric coils to begin heating an interior of the holding wherein drying the face mask. The processor stops the stepper motor wherein retaining the pair of fins in a fixed position before actuating a door motor. The door motor engages with a hinge of a door to position the door from a closed position to an open position wherein removing the face mask from the holding. The user collects the face mask from the outlet of front surface of the housing.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
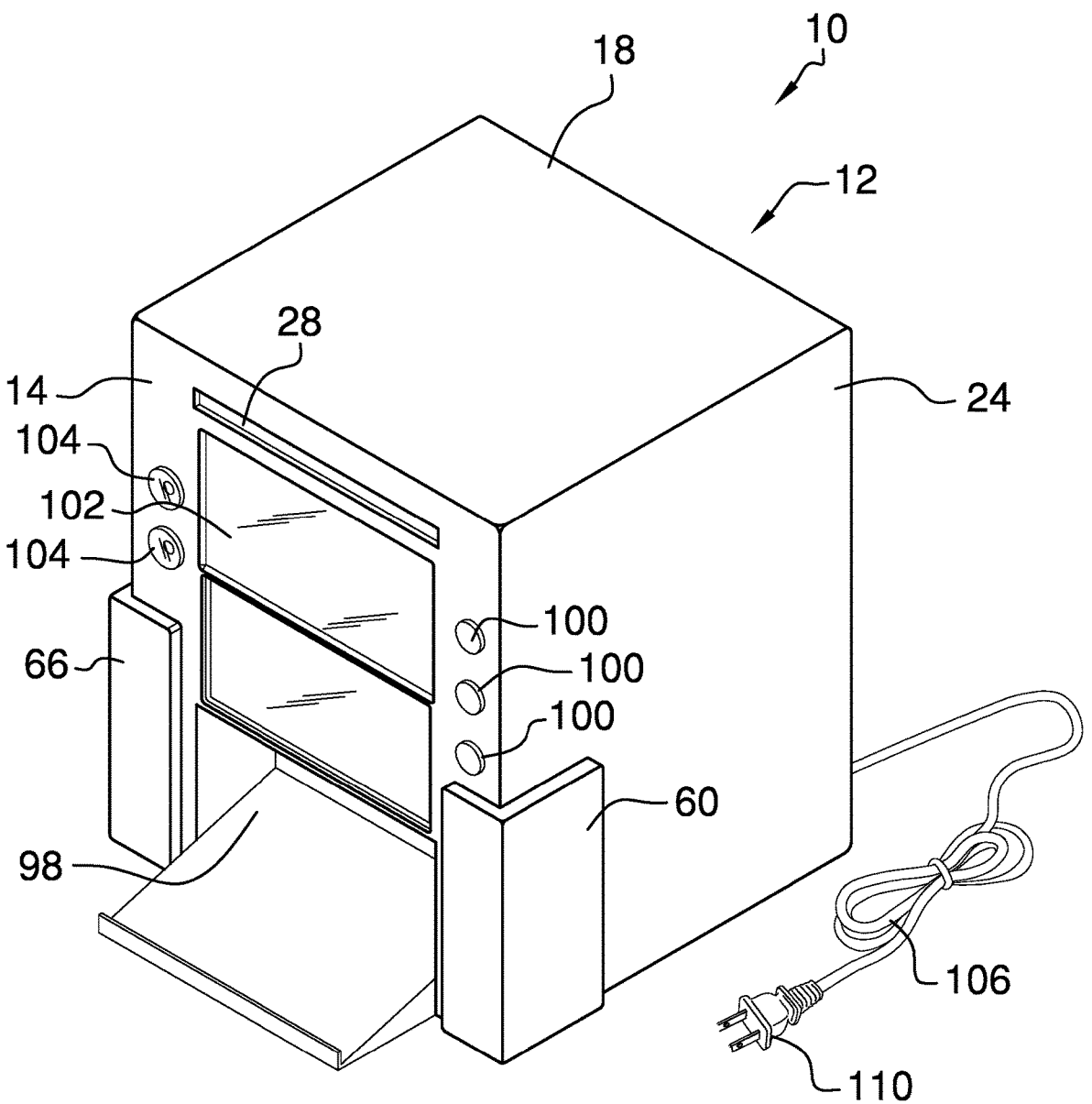
FIG. 1 is a top isometric view of a portable mask cleaning device according to an embodiment of the disclosure.
Figure 2:
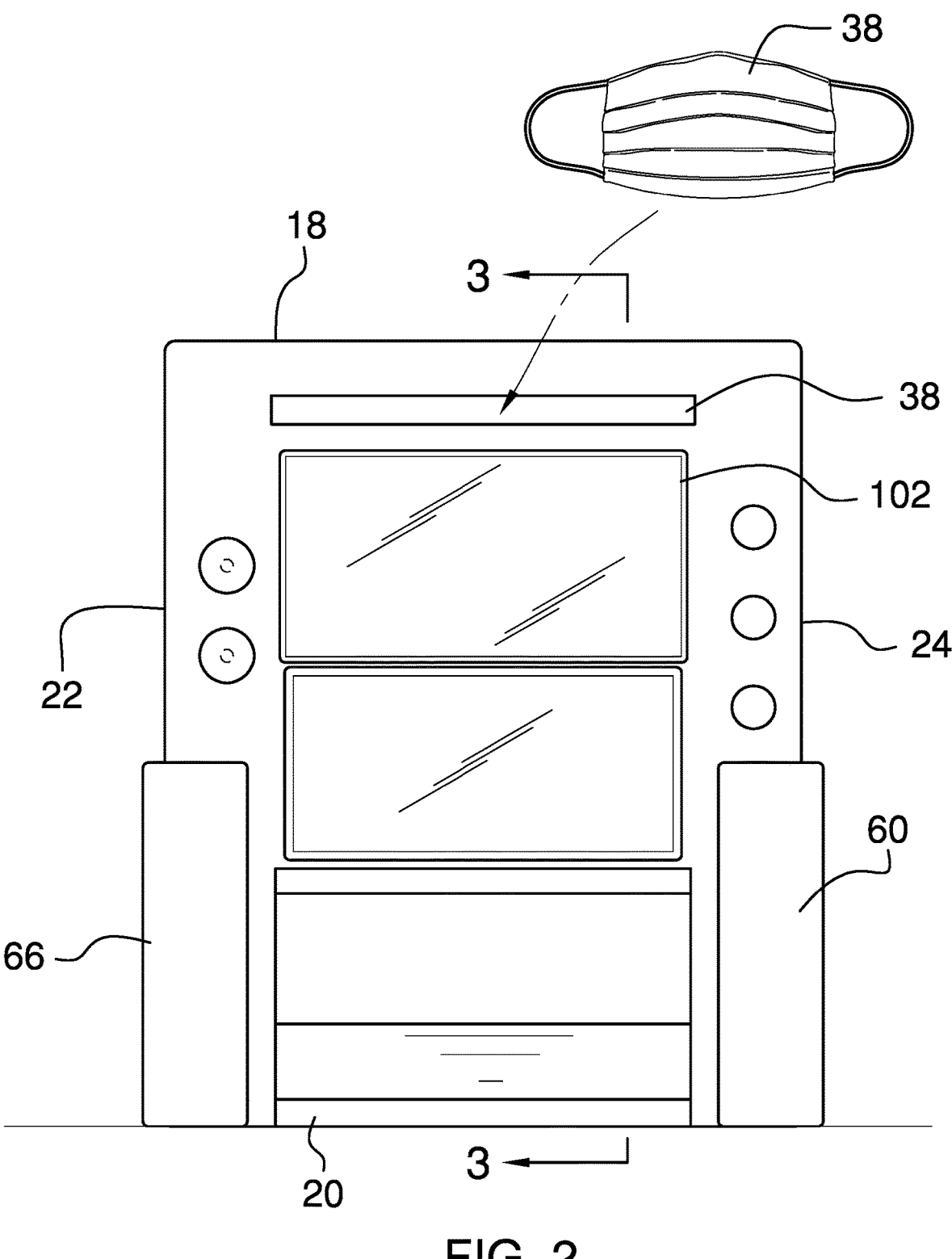
FIG. 2 is a front view of an embodiment of the disclosure.
Figure 3:
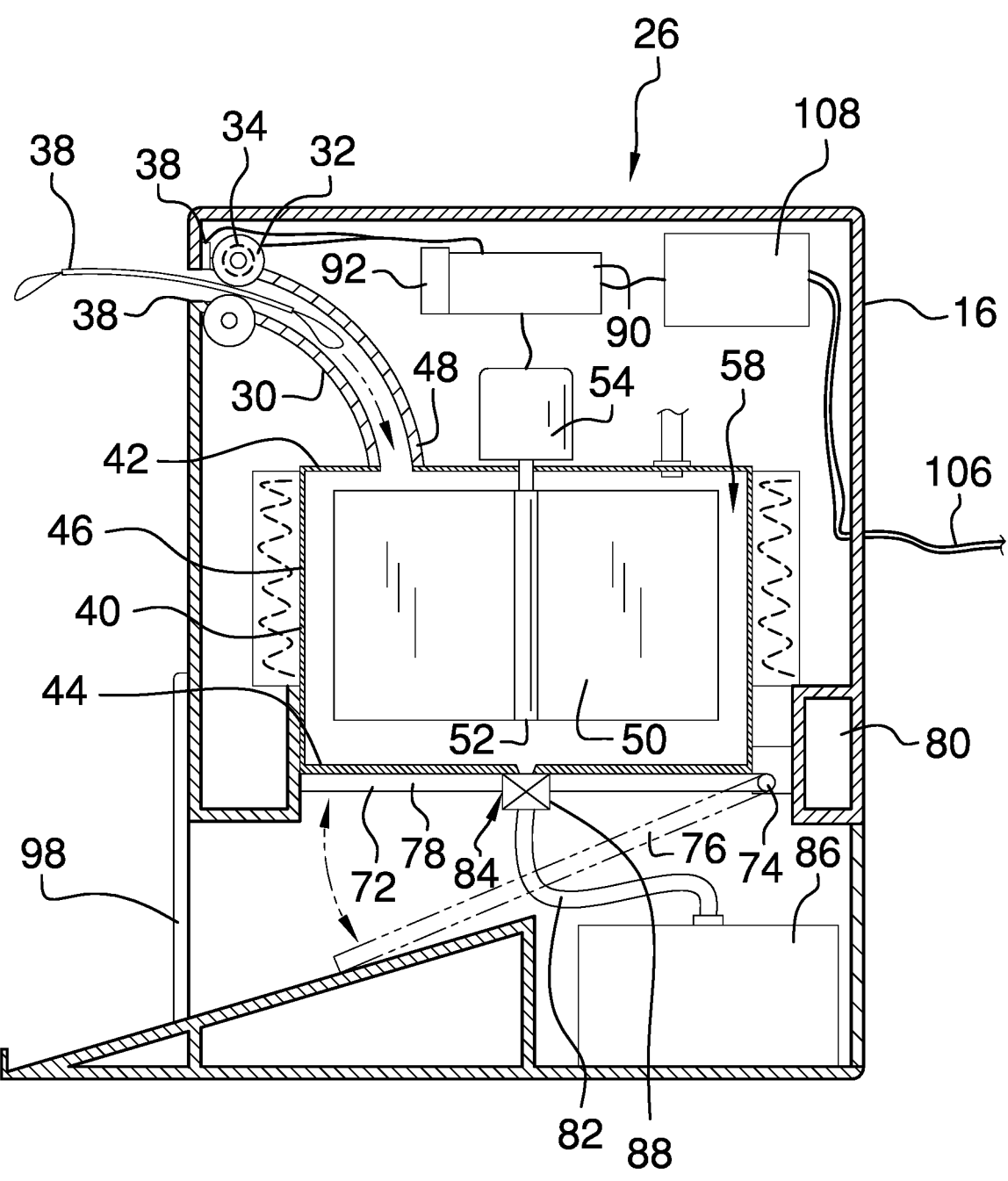
FIG. 3 is a cross-sectional view of an embodiment of the disclosure taken from FIG. 2 of Line 3-3.
Figure 4:
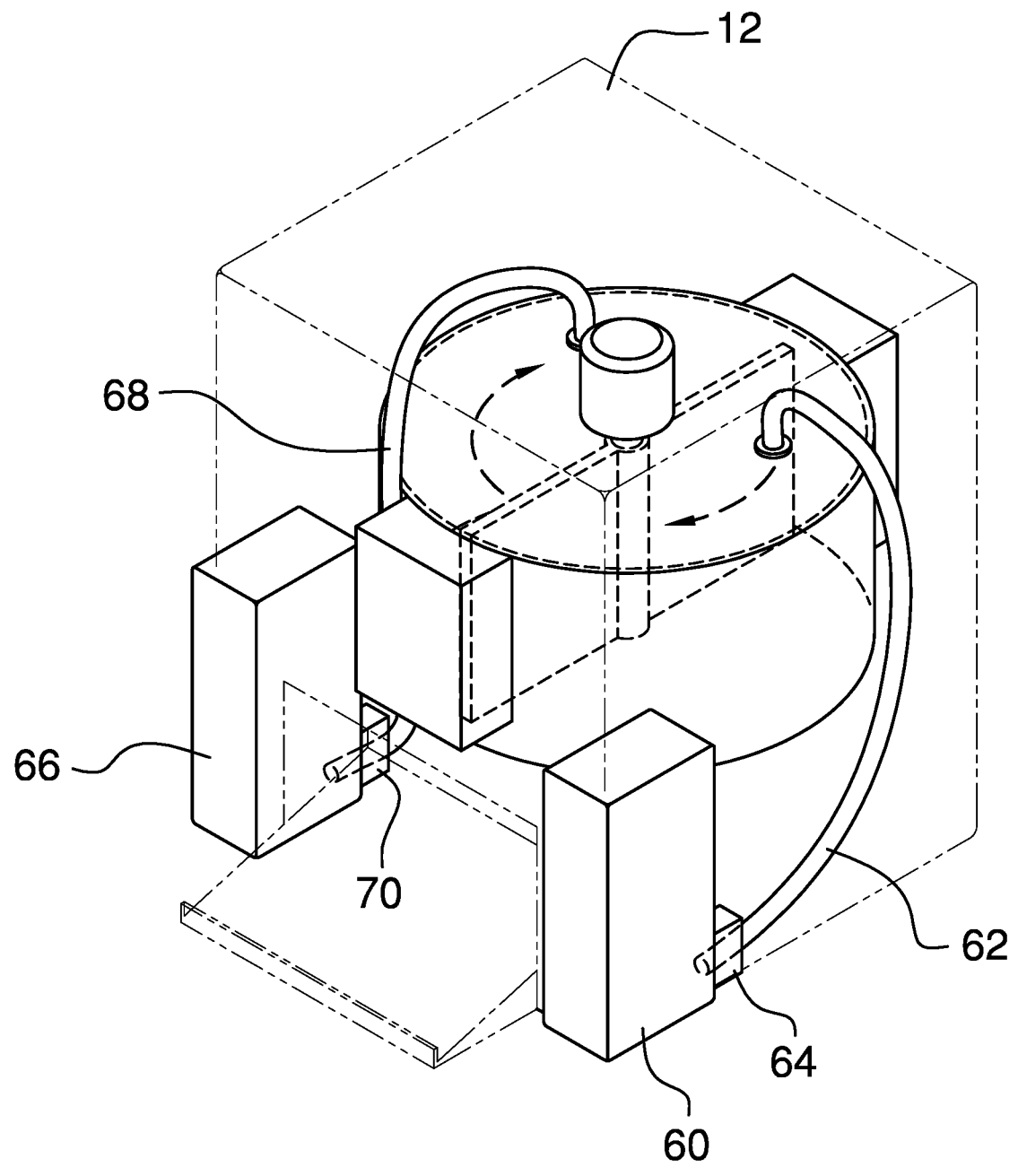
FIG. 4 is a detail view of an embodiment of the disclosure.
Figure 5:
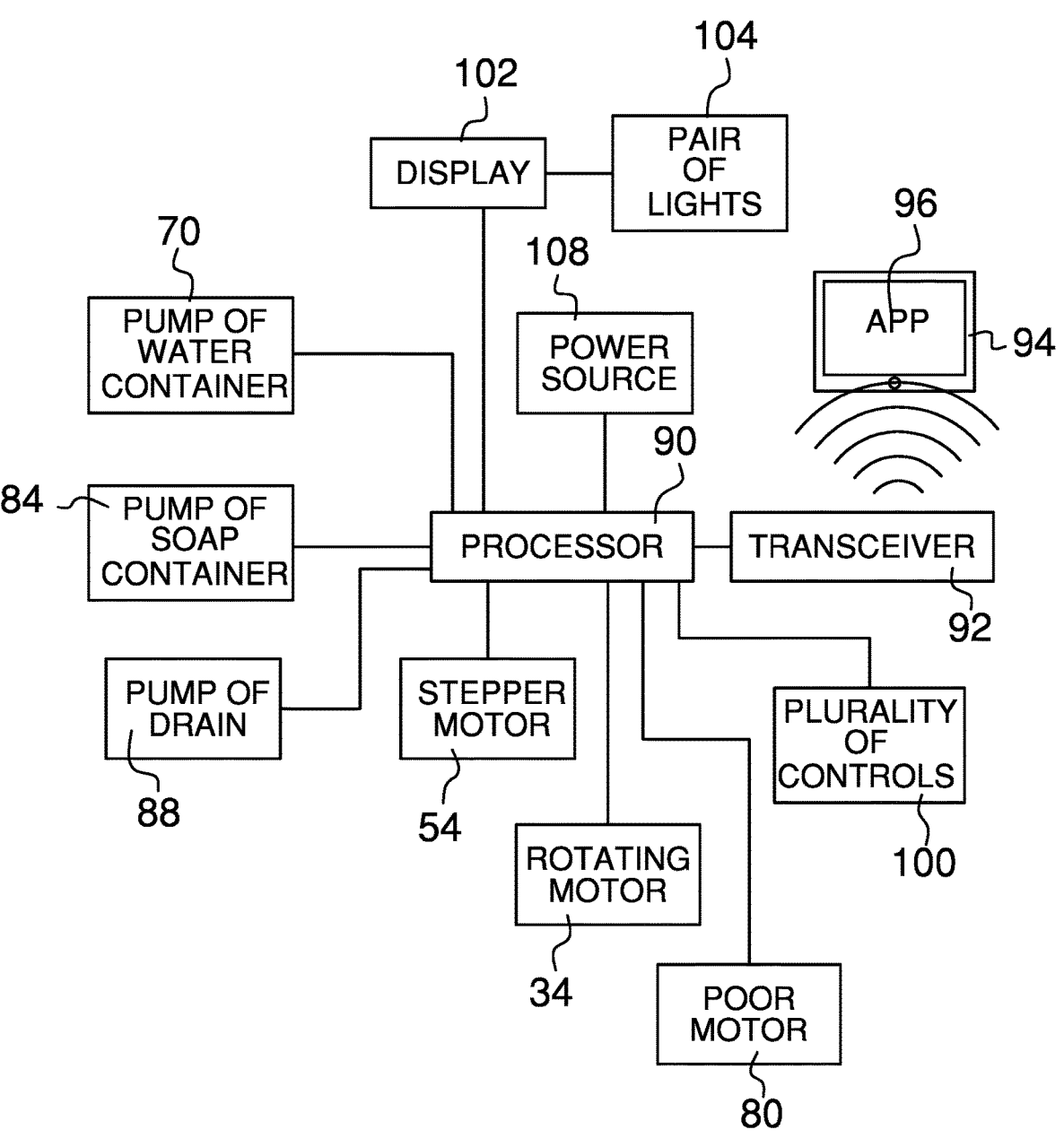
FIG. 5 is a block diagram view of an embodiment of the disclosure.

With reference now to the drawings, and in particular to FIGS. 1 through 5 thereof, a new clothing wash device embodying the principles and concepts of an embodiment of the disclosure and generally designated by the reference numeral 10 will be described.

As best illustrated in FIGS. 1 through 5, the portable mask cleaning device 10 generally comprises a housing 12. The housing 12 has a front surface 14 and a back surface 16 positioned parallel to each other. The housing 12 has a top surface 18 and a bottom surface 20 positioned parallel relative to each other. Additionally, the housing 12 has a left surface 22 and a right surface 24 wherein each of the surfaces enclosing an interior 26. The interior 26 defines a space for a variety of elements to be positioned within. The positioning of each of the surfaces relative to each other produces a rectangular prism shape of the housing 12.

A slot 28 is positioned on the front surface 14 and proximate to the top surface 18 of the housing 12. The slot 28 is an opening to the interior 26 of the housing 12. The slot 28 is slimmed to reduced unwanted items entering the interior 26. A conduit 30 protrudes out from the slot 28 into the interior 26 of the housing 12. The conduit 30 has a pair of rollers 32 wherein each of the rollers 32 is coupled to a rotating motor 34. The rotating motor 34 is in electric communication to a motion sensor 36 positioned adjacent to the slot 28 of the housing 12. Each of the rollers 32 is configured for moving a face mask 38 through the conduit 30. The motion sensor 36 actuates the rotating motor 34 when the face mask 38 enters the slot 28.

A holding 40 is positioned within the interior 26 of the housing 12. The holding 40 has a top wall 42 and a bottom wall 44. A perimeter wall 46 is positioned between the top 42 and bottom 44 walls of the holding 40 and is a circular shape. An end 48 of the conduit 30 is positioned on the top wall 42 of the holding 40, wherein the holding 40 is configured for storing the face mask 38 from the conduit 30. A pair of fins 50 is positioned within the holding 40. The pair of fins 50 is coupled to a rod 52, wherein the rod 52 is coupled to a stepper motor 54. The stepper motor 54 is positioned proximate to the top wall 42 of the holding 40 and is configured for rotating the pair of fins 50 within the holding 40. Furthermore, a pair of electric coils 56 is positioned adjacent to the perimeter wall 46 of the holding 40. Each of the electric coils 56 is configured for heating an interior 58 of the holding 40. By heating the interior 58 of the holding 40, the face mask 38 within the holding 40 is heated as well.

A soap container 60 is positioned adjacent to the front surface 14 and the right surface 24 of the housing 12. The soap container 60 is configured for holding laundry soap to clean the face mask 38. The soap container 60 has a tube 62 protruding out from the soap container 60 into the top wall 42 of the holding 40. The tube 62 of the soap container 60 has a pump 64 being configured for flowing laundry soap to the holding 40. In addition to the soap container 60, a water container 66 is positioned adjacent to the front surface 14 and the left surface 22 of the housing 12. The water container 66 is configured for holding water. The water container 66 has a tube 68 protruding out from the water container 66 into the top wall 42 of the holding 40. The tube 68 of the water container 66 has a pump 70 being configured for flowing water to the holding 66.

A door 72 is coupled to the bottom wall 44 of the holding 40. The door 72 has a hinge 74 being configured for positioning the door 72 in an open 76 and closed 78 position relative to the holding 40. The hinge 74 has a door motor 80 being configured for opening and closing the door 72. Additionally, a drain 82 is positioned in a center 84 of the door 72. The drain 82 is a conduit from the door 72 to a reservoir 86. The drain 82 has a pump 88 being configured for flowing a fluid within the holding 40 to the reservoir 86. The reservoir 86 is positioned below the holding 40 of the interior 26 of the housing 12 to optimize the process of draining the fluid within the holding 40 by the use of gravitational force.

A processor 90 is positioned within the interior 26 of the housing 12. The processor 90 is in electric communication with the door motor 80, the rotating motor 34, and the stepper motor 54. The processor 90 is in electric communication with the pair of electric coils 56 as well. Additionally, the processor 90 is in electric communication with the pump 88 of the drain 82, the pump 64 of the soap container 60, and the pump 70 of the water container 66. The processor 90 is configured for rendering data and performing operations of within the interior of the housing 12. A transceiver 92 is in electric communication with the processor 90. The transceiver 92 is configured for being in wireless communication with an application 96 of a mobile device 94 wherein the mobile device 94 actuates the processor 90 of the housing 12 by the application 96.

An outlet 98 is positioned on the front surface 14 and proximate to the bottom surface 20 of the housing 12. The outlet 98 is an opening to the door 72 of the holding 40 of the interior 26 of the housing 12. The outlet 98 provides a space for the user to obtain the face mask 38 after being washed and dried. A plurality of controls 100 is positioned on the front surface 14 of the housing 12. Each of the controls 100 is in electric communication with the processor 90 wherein each of the controls 100 is an actuator for the processor 90. In addition, a display 102 is positioned on the front surface 14 of the housing 12. The display 102 is a screen configured for displaying a timer of the processor 90. The display 102 has a pair of lights 104 wherein each of the lights 104 is configured for indicating a status of the processor 90.

A power cord 106 is in electric communication with a power source 108. The power cord 106 is positioned on the back surface 16 of the housing 12 and protrudes out from the back surface 16. The power cord 106 has an outlet plug 110 being configured for being inserted into a power outlet. The power source 108 of the power cord 106 is configured for providing electric power to the processor 90.

In use, the user plugs the outlet plug 110 of the power cord 106 into a power outlet. The user inserts the face mask 38 within the slot 28 of the front surface 14 of the housing 12. The pair of rollers 32 moves the face mask 38 through the conduit 30 to the holding 40 within the interior 26 of the housing 12. The user actuates the processor 90 using either the plurality of controls 100 or the application 96 of the mobile device 94 communicating with the transceiver 92 of the processor 90. The actuation of the processor 90 includes the step of actuating the pump 64 of the tube 62 of the soap container 60 to flow laundry detergent into the holding 40. Additionally, the processor 90 actuates the pump 70 of the tube 68 of the water container 66 to flow water into the holding 40. The processor 90 actuates the stepper motor 54 of the pair of fins 50 within the holding 40. The stepper motor 54 rotates the pair of fins 50 within the holding 40 wherein washing the face mask 38. The processor 90 removes the fluid from the holding 40 by actuating the pump 88 of the drain 82 to the reservoir 86. Subsequently, the processor 90 actuates the pair of electric coils 56 to begin heating the interior 58 of the holding 40 wherein drying the face mask 38. The processor 90 stops the stepper motor 54 wherein retaining the pair of fins 50 in a fixed position before actuating the door motor 80. The door motor 80 engages with the hinge 74 of the door 72 to position the door 72 from the closed position 78 to the open position 76 wherein removing the face mask 38 from the holding 40. The user collects the face mask 38 from the outlet 98 of front surface 14 of the housing 12.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A portable mask cleaning device configured for washing and drying a face mask, the portable mask cleaning device comprising:
   a housing having a front surface and a back surface positioned parallel relative to each other, said housing having a left surface and a right surface, said housing enclosing an interior;
   a slot being positioned on said front surface of said housing;
   a conduit protruding out from said slot into said interior of said housing, said conduit having a pair of rollers, each of said rollers being configured for moving a face mask through said conduit;
   a holding being positioned within said interior of said housing, said holding having a top wall and a bottom wall, said holding having a perimeter wall, said holding being configured for storing the face mask;
   a pair of fins being positioned within said holding, said pair of fins being coupled to a rod, said rod being coupled to a stepper motor, said stepper motor being configured for rotating said pair of fins within said holding;
   a pair of electric coils being positioned adjacent to said perimeter wall of said holding, each of said electric coils being configured for heating an interior of said holding;
   a soap container being positioned adjacent to said front surface and said right surface of said housing, said soap container having a soap container tube, said soap container tube protruding out from said soap container into said top wall of said holding;
   a water container being positioned adjacent to said front surface and said left surface of said housing, said water container having a water container tube, said water container tube protruding out from said water container into said top wall of said holding;
   a door being coupled to said bottom wall of said holding;
   a drain being positioned in a center of said door, said drain being a conduit from said door to a reservoir;
   a processor being positioned within said interior of said housing, said processor being configured for operating the portable mask cleaning device;
   an outlet being positioned on the front surface of said housing, said outlet being an opening to said door of said holding of said interior of said housing; and
   a power cord being in electric communication with a power source, said power source of said power cord being configured for providing electric power to said processor.

2. The portable mask cleaning device of claim 1, further comprising said housing having a top surface and a bottom surface positioned parallel relative to each other, said interior defining a space for a variety of elements to be positioned within.

3. The portable mask cleaning device of claim 2, further comprising said slot being positioned proximate to said top surface of said housing.

4. The portable mask cleaning device of claim 2, further comprising said outlet being positioned proximate to said bottom surface of said housing.

5. The portable mask cleaning device of claim 1, further comprising each of said rollers being coupled to a rotating motor, said rotating motor being in electric communication to a motion sensor, said motion sensor being positioned adjacent to said slot of said housing.

6. The portable mask cleaning device of claim 1, further comprising said perimeter wall being a circular shape, an end of said conduit being positioned on said top wall of said holding, said holding being configured for storing a face mask.

7. The portable mask cleaning device of claim 6, further comprising said stepper motor being positioned proximate to said top wall of said holding.

8. The portable mask cleaning device of claim 7, further comprising said soap container being configured for holding laundry soap, said soap container tube having a pump, said pump of said soap container tube being configured for flowing said laundry soap to said holding.

9. The portable mask cleaning device of claim 8, further comprising said water container being configured for holding water, said water container tube having a pump, said pump of said water container tube being configured for flowing said water to said holding.

10. The portable mask cleaning device of claim 9, further comprising said door having a hinge, said hinge being configured for positioning said door in an open and closed position relative to said holding, said hinge having a door motor, said door motor being configured for opening and closing said door.

11. The portable mask cleaning device of claim 10, further said drain having a pump, said pump of said drain being configured for flowing a fluid within said holding to said reservoir.

12. The portable mask cleaning device of claim 11, further comprising said processor being in electric communication with said door motor and said rotating motor and said stepper motor, said processor being in electric communication with said pair of electric coils, said processor being in electric communication with said pump of said drain and said pump of said soap container and said pump of said water container.

13. The portable mask cleaning device of claim 12, further comprising a transceiver being in electric communication with said processor, said transceiver being configured for being in wireless communication with an application of a mobile device wherein said mobile device actuates said processor of said housing.

14. The portable mask cleaning device of claim 12, further comprising a plurality of controls being positioned on said front surface of said housing, each of said controls being in electric communication with said processor, each of said controls being an actuator for said processor.

15. The portable mask cleaning device of claim 14, further comprising a display being positioned on said front surface of said housing, said display being a screen configured for displaying a timer of said processor, said display having a pair of lights, each of said lights being configured for indicating a status of said processor.

16. The portable mask cleaning device of claim 15, further comprising said power cord being positioned on said back surface of said housing, said power cord having a outlet plug.

17. A portable mask cleaning device configured for washing and drying a face mask, the portable mask cleaning device comprising:

a housing having a front surface and a back surface positioned parallel relative to each other, said housing having a top surface and a bottom surface positioned parallel relative to each other, said housing having a left surface and a right surface, said housing enclosing an interior, said interior defining a space for a variety of elements to be positioned within;

a slot being positioned on said front surface of said housing, said slot being positioned proximate to said top surface of said housing, said slot being an opening to said interior of said housing;

a conduit protruding out from said slot into said interior of said housing, said conduit having a pair of rollers, each of said rollers being coupled to a rotating motor, said rotating motor being in electric communication to a motion sensor, said motion sensor being positioned adjacent to said slot of said housing, each of said rollers being configured for moving a face mask through said conduit;

a holding being positioned within said interior of said housing, said holding having a top wall and a bottom wall, said holding having a perimeter wall, said perimeter wall being a circular shape, an end of said conduit being positioned on said top wall of said holding, said holding being configured for storing the face mask;

a pair of fins being positioned within said holding, said pair of fins being coupled to a rod, said rod being coupled to a stepper motor, said stepper motor being positioned proximate to said top wall of said holding, said stepper motor being configured for rotating said pair of fins within said holding;

a pair of electric coils being positioned adjacent to said perimeter wall of said holding, each of said electric coils being configured for heating an interior of said holding;

a soap container being positioned adjacent to said front surface and said right surface of said housing, said soap container being configured for holding laundry soap, said soap container having a soap container tube, said soap container tube protruding out from said soap container into said top wall of said holding, said soap container tube having a pump, said pump of said soap container tube being configured for flowing said laundry soap to said holding;

a water container being positioned adjacent to said front surface and said left surface of said housing, said water container being configured for holding water, said water container having a water container tube, said water container tube protruding out from said water container into said top wall of said holding, said water container tube having a pump, said pump of said water container tube being configured for flowing said water to said holding;

a door being coupled to said bottom wall of said holding, said door having a hinge, said hinge being configured for positioning said door in an open and closed position relative to said holding, said hinge having a door motor, said door motor being configured for opening and closing said door;

a drain being positioned in a center of said door, said drain being a conduit from said door to a reservoir, said drain having a pump, said pump of said drain being configured for flowing a fluid within said holding to said reservoir;

a processor being positioned within said interior of said housing, said processor being in electric communication with said door motor and said rotating motor and said stepper motor, said processor being in electric communication with said pair of electric coils, said processor being in electric communication with said pump of said drain and said pump of said soap container and said pump of said water container, said processor being configured for operating the portable mask cleaning device;

a transceiver being in electric communication with said processor, said transceiver being configured for being in wireless communication with an application of a mobile device wherein said mobile device actuates said processor of said housing;

an outlet being positioned on the front surface of said housing, said outlet being positioned proximate to said bottom surface of said housing, said outlet being an opening to said door of said holding of said interior of said housing;

a plurality of controls being positioned on said front surface of said housing, each of said controls being in electric communication with said processor, each of said controls being an actuator for said processor;

a display being positioned on said front surface of said housing, said display being a screen configured for displaying a timer of said processor, said display having a pair of lights, each of said lights being configured for indicating a status of said processor; and a power cord being in electric communication with a power source, said power cord being positioned on said back surface of said housing, said power cord having a outlet plug, said power source of said power cord being configured for providing electric power to said processor.

* * * * *